(12) United States Patent
Hardy et al.

(10) Patent No.: US 6,376,171 B1
(45) Date of Patent: Apr. 23, 2002

(54) METHODS OF SCREENING FOR ANTIVIRAL COMPOUNDS

(75) Inventors: Richard W. Hardy, Maplewood, MO (US); Gail W. Wertz, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/511,023

(22) Filed: Feb. 23, 2000

Related U.S. Application Data

(60) Provisional application No. 60/122,251, filed on Feb. 26, 1999.

(51) Int. Cl.[7] .............................. C12Q 1/70; C12Q 1/00; G01H 33/567
(52) U.S. Cl. ...................... 435/5; 435/4; 435/3; 435/7.2
(58) Field of Search ............................... 435/5, 3, 4, 7.2

(56) References Cited

U.S. PATENT DOCUMENTS

| | | | |
|---|---|---|---|
| 5,256,668 A | * 10/1993 | Hsu et al. | 514/269 |
| 6,001,555 A | * 12/1999 | Henderson et al. | 435/5 |
| 6,017,694 A | * 1/2000 | Mak et al. | 435/5 |

OTHER PUBLICATIONS

Hardy et al. Jan. 1998. The product of the respiratory syncytial virus M2 gene ORF1 enhances readthrough of intergenic junctions during viral transcription. J. of Virology. vol. 72 (1); 520–526.*

Hu et al. 1989. Evalution of new antiviral agents: I. In vitro perspectives. Antiviral research. vol. 11; 217–232.*

Prusoff et al. 1986. Potential targets for antiviral chemotherapy. Antiviral Research. vol. 6; 311–328.*

Fields et al. 1995. Virology, 3rd edition. Lippencott Williams and Wilkins publishers. vol. 1, p. 1322.*

Collins et al. 1995. Production of infectious respiratory syncytial virus from cloned cDNA confirms an essential role for the transcription elongation factor from the 5' proximal open reading frame of the M2 mRNA in gene expression and provides a capability for vaccine development. PNAS. vol. 92:11563–11567.

* cited by examiner

*Primary Examiner*—James Housel
*Assistant Examiner*—Shanon A. Foley
(74) *Attorney, Agent, or Firm*—Benjamin Aaron Adler

(57) ABSTRACT

The present invention demonstrates that the M2-1 protein of respiratory syncytial virus has a conserved $Cys_3$-$His_1$ motif known to bind zinc ions in other proteins and that mutations of the predicted zinc coordinating residues in the $Cys_3$-$His_1$ motif affect the transcriptional antitermination activity of M2-1, its ability to interact with nucleocapsid protein, and the phosphorylation state of M2-1. This invention clearly demonstrates the requirement for conservation of the $Cys_3$-$His_1$ motif in order to maintain the functional integrity of the M2-1 protein. Therefore, the present invention provides for methods of designing and screening compounds for antiviral activity towards respiratory syncytial virus based upon the loss of function of the M2-1 protein.

15 Claims, 9 Drawing Sheets

METHODS OF SCREENING FOR ANTIVIRAL COMPOUNDS

CROSS-REFERENCE TO RELATED APPLICATIONS

This non-provisional application claims benefit of priority under 35 U.S.C. 119(e) of U.S. provisional application No. 60/122,251 filed Feb. 26, 1999, now abandoned.

This patent application claims benefit of provisional patent application U.S. Ser. No. 60/122,251, filed Feb. 26, 1999.

FEDERAL FUNDING LEGEND

This invention was produced in part using funds obtained through grants AI12464 and AI20181 from the National Institute of Health. Consequently, the federal government has certain rights in this invention.

BACKGROUND OF THE INVENTION

1. Field of the Invention

The present invention relates generally to the field of virology and to the process and control of viral RNA transcription. More specifically, the present invention relates to a $Cys_3$-$His_1$ motif within the M2-1 protein of respiratory syncytial virus and the use of this functional motif as a target for screening of antiviral agents.

2. Description of the Related Art

Human respiratory syncytial (RS) virus is a member of the pneumovirus genus of the Paramyxoviridae. It is the leading viral cause of pediatric lower respiratory tract disease and is a significant cause of morbidity and mortality worldwide. The genome of RS virus is a single strand of negative-sense RNA 15,222 nucleotides in length having 10 genes encoding 11 proteins (4, 15, 25, 33). As with all nonsegmented, negative-sense RNA viruses, RNA synthesis requires a genomic RNA encapsidated with nucleocapsid (N) protein and the virus encoded components of the RNA dependent RNA polymerase, the phosphoprotein (P) and the large polymerase protein (L) (7, 38). The N, P and L proteins are sufficient for replication of the genomic RNA (10, 38). However, RS virus, unlike other nonsegmented negative-sense RNA viruses, encodes an additional protein, M2-1, which functions during transcription of the viral mRNAs (3). This protein has been shown to increase the processivity of the viral polymerase thus preventing premature termination during transcription. Additionally it has been shown that the M2-1 protein enhances readthrough of transcription termination signals and thus functions as a transcription antiterminator (8, 13). Furthermore, the RS virus gene end sequences vary and it has been shown that the M2-1 protein acts differentially at the different gene ends (11).

The M2-1 protein is found only in pneumoviruses. It is encoded by the first of two open reading frames (ORF) in the next to last gene of the RS virus genome and is 194 amino acids in length (calculated m.w.=22,150 daltons) (5). M2-1 is a hydrophilic protein with a predicted pI of 9.6. Examination of the predicted amino acid sequence led to the identification of a $Cys_3$-$His_1$ motif (C—$X_7$—C—$X_5$—C—$X_3$—H) located near the amino terminus of the protein from residues 7 to 25. This motif is found in the M2-1 protein of all the pneumoviruses examined to date (12, 20, 37, 39). A similar motif is found in VP30 of the filoviruses (29). A number of motifs have been characterized as coordinating the binding of zinc. These motifs have been grouped according to the arrangement and number of cysteine and histidine residues involved in coordinating the zinc ion. Many proteins bind zinc, and, in a number of enzymes, zinc has been shown to play a role in catalysis (16). However, in other cases, zinc plays a purely structural role (24). The $Cys_3$-$His_1$ motif has been characterized in only one protein, Nup475, a mammalian transcription factor in which it was demonstrated to bind zinc and a structure for this motif has been proposed using NMR and photometric analyses (36).

Six species of the RS virus M2-1 protein have been observed by two-dimensional electrophoresis (27). When the M2-1 protein was analyzed by SDS-PAGE under reducing conditions, the majority of the protein was found in two forms distinguished by their electrophoretic mobility. The cause of the differences in migration of these species or whether the different species have different functions is unknown. The M2-1 protein has been reported to be phosphorylated, but the relationship between phosphorylation and the different forms of the protein has not been investigated (18).

The M2-1 protein has also been shown to interact with the N protein in RS virus-infected cells or when the two proteins are coexpressed in cells from plasmid vectors (9, 28). The significance of this interaction and the role it may play is currently unknown.

The prior art is deficient in methods of screening for antiviral compounds that are specific for respiratory syncytial virus. The present invention fulfills this long-standing need and desire in the art.

SUMMARY OF THE INVENTION

In the instant invention the role of the predicted zinc coordinating residues of the $Cys_3$-$His_1$ motif in the antitermination activity of M2-1 protein, in its ability to interact with N protein, and in its phosphorylation state were examined. It was found that mutations of the residues predicted to coordinate zinc prevented the M2-1 protein from enhancing transcriptional readthrough and interacting with the nucleocapsid protein. It was also found that the two major species of the M2-1 protein distinguished by their mobility in reducing SDS-PAGE differed according to whether they were phosphorylated. This work demonstrates the requirement for conservation of the $Cys_3$-$His_1$ motif, a potential zinc binding domain, to maintain the functional integrity of the M2-1 protein.

One object of the present invention is to provide a method of screening for antiviral compounds specific for respiratory syncytial virus.

In one embodiment of the present invention, there is provided a method of screening for antiviral compounds directed towards respiratory syncytial virus, comprising the steps of: a) treating a sample of respiratory syncytial virus with a compound, thereby producing a treated sample and an untreated sample; b) producing respiratory syncytial virus RNA transcripts in the presence of said treated sample or in the presence of said untreated sample; and c) comparing said transcripts produced in the presence of said treated sample with said transcripts produced in the presence of said untreated sample, wherein less readthrough transcripts due to termination at gene end signal produced in the presence of said treated sample is indicative of an antiviral compound directed towards respiratory syncytial virus.

In another embodiment of the present invention, there is provided a method of screening for antiviral compounds directed towards respiratory syncytial virus, comprising the steps of: a) treating a sample of respiratory syncytial virus with a compound, thereby producing a treated sample and an untreated sample; and b) comparing the treated sample with an untreated sample, wherein an inhibitory effect on the treated sample compared to the untreated sample of a characteristic such as M2-1 transcriptional antitermination, zinc binding, phosphorylation, binding to respiratory syncytial virus N protein, viral transcription or generation of progeny virus particles is indicative of a compound with antiviral activity.

In another embodiment of the present invention, there is provided a method of screening for antiviral compounds directed towards respiratory syncytial virus, comprising the steps of: a) treating a sample of respiratory syncytial virus with a chelator or a compound that inhibits binding of Zinc; and b) comparing the treated sample with an untreated sample, wherein an inhibitory effect on the treated sample compared to the untreated sample of a characteristic such as M2-1 transcriptional antitermination, zinc binding, phosphorylation, binding to respiratory syncytial virus N protein, viral transcription or generation of progeny virus particles is indicative of a compound with antiviral activity.

In yet another embodiment of the present invention, there is provided a method of screening antiviral compounds directed towards respiratory syncytial virus, comprising the steps of: a) treating a sample of respiratory syncytial virus selected from the group consisting of core polymerase protein, nucleocapsid protein, phosphoprotein, an isolated virus or a virus-infected cell with a compound, thereby producing a treated sample and an untreated sample; and b) producing respiratory syncytial virus RNA transcripts in the presence of said treated sample or in the presence of said untreated sample, wherein an inhibition of virus RNA transcription or production of progeny virus particles in the presence of said treated sample is indicative of an antiviral compound directed towards respiratory syncytial virus.

In yet another embodiment of the present invention, there is provided a method of designing antiviral compounds directed towards respiratory syncytial virus, comprising the steps of: a) designing a compound that inhibits zinc binding to a $Cys_3$-$His_1$ motif of a respiratory syncytial virus M2-1 protein; b) treating a sample of respiratory syncytial virus with said designed compound; and c) comparing said treated sample with said untreated sample, wherein an inhibitory effect on said treated sample, when compared to the untreated sample, of a characteristic such as M2-1 transcriptional antitermination, zinc binding, phosphorylation, binding to respiratory syncytial virus N protein, viral transcription or generation of progeny virus particles is indicative of a compound with antiviral activity. A preferred method of designing is by computer modeling.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore should not be considered to limit the scope of the invention.

FIG. 1 shows the effects of mutations in the $Cys_3$-$His_1$ motif of the M2-1 protein on RS virus transcription.

HEp-2 cells infected with vTF7-3 were transfected with pN alone (lane 1) or pN and plasmids encoding wild-type or mutated M2-1 proteins as indicated (lanes 2 to 6). Cells were exposed to [$^{35}$S]-methionine and cysteine for 2 h at 16 h post-transfection. Labeled proteins were immunoprecipitated from cytoplasmic extracts using M2-1 specific MAb 5H5. Immunoprecipitated proteins were analyzed by SDS-PAGE in 11% polyacrylamide gels followed by fluorography. Positions of the M2-1 and N proteins are indicated. wt, wild-type.

Figure 6:
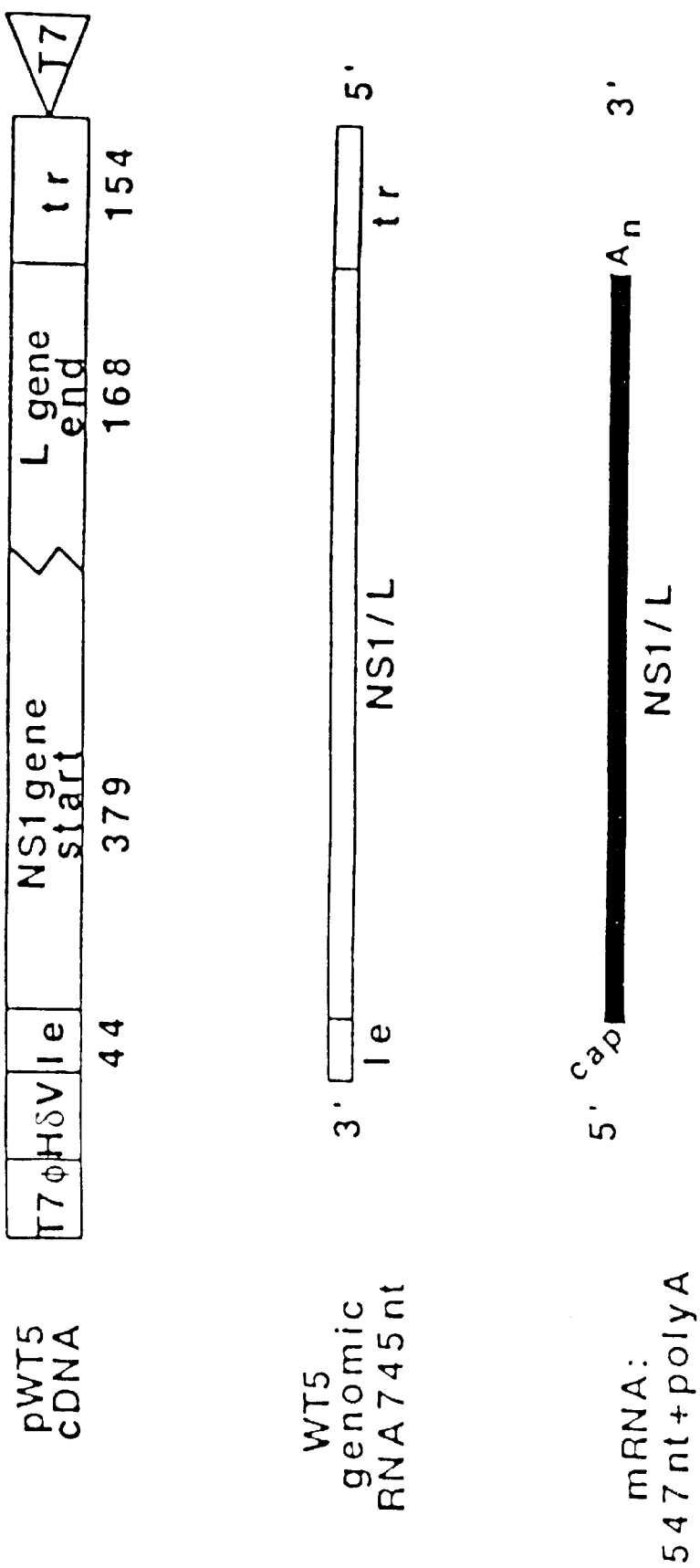

FIG. 6 shows a diagram of plasmid pWT5 and the RNAs predicted to be synthesized from the monocistronic subgenomic replicon that it encodes. The subgenomic replicon transcribed from pWT5 includes the RS virus 3' and 5' termini flanking a fused partial NS1 and L gene. Thus, transcription by T7 polymerase followed by self-cleavage gave rise to a negative-sense copy of the subgenomic replicon RNA. This RNA can act as a template from which the RS virus RNA polymerase can synthesize a 547-nucleotide (nt) mRNA (not including the poly(A) tail) or a positive-sense product of replication. tr, trailer.

Figure 7:
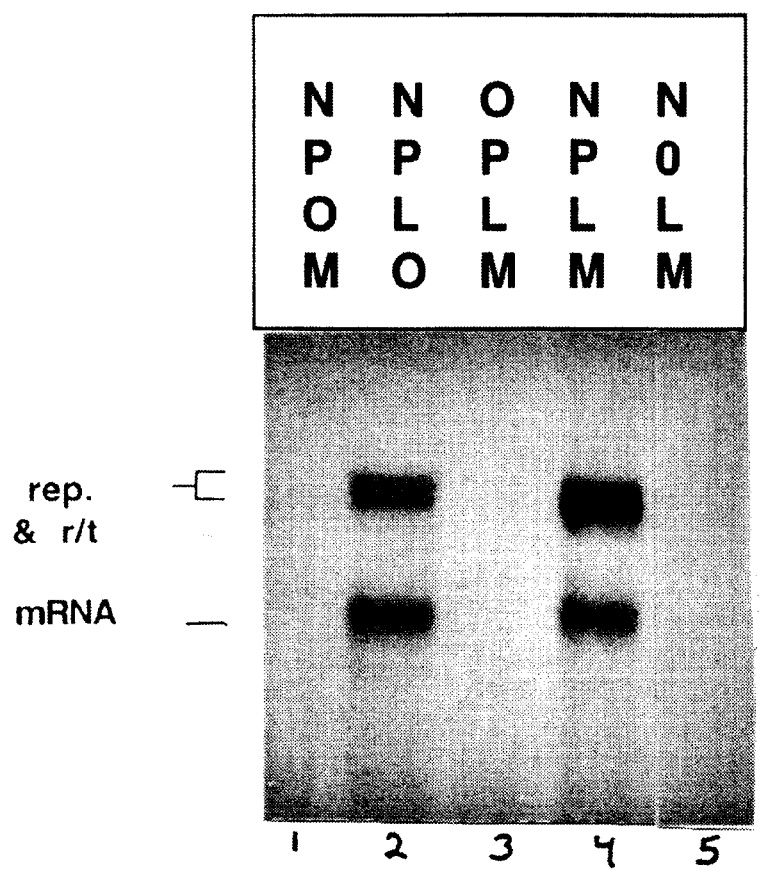

FIG. 7 shows the products of RNA synthesis from WT5 subgenomic replicon. Cells were infected with vTF7-3, transfected with cDNAs pWT5, pN, pP, pL and pM2-1 as indicated, and exposed to [$^3$H]uridine in the presence of actinomycin D. "O" indicated that a particular plasmid has been omitted.

DETAILED DESCRIPTION OF THE INVENTION

The M2 gene of respiratory syncytial (RS) virus has two open reading frames (ORFs). ORF1 encodes a 22 kDa protein termed M2-1. The M2-1 protein contains a $Cys_3$-$His_1$ motif (C—$X_7$—C—$X_5$—C—$X_3$—H) near the amino terminus. This motif is conserved in all strains of human, bovine and ovine species of RS virus. A similar motif found in the mammalian transcription factor Nup475 has been shown to bind zinc. The M2-1 protein of human RS virus functions as a transcription factor which increases polymerase processivity and it enhances readthrough of intergenic junctions during RS virus transcription thereby acting as a transcription antiterminator. The M2-1 protein also interacts with the nucleocapsid protein. The effects of mutations of cysteine and histidine residues predicted to coordinate zinc in the $Cys_3$-$His_1$ motif of M2-1 protein on transcription antitermination and N protein binding were examined. It was found that mutating the predicted zinc coordinating residues, the cysteine residues at amino acid positions 7 and 15 or the histidine residue at position 25, prevented M2-1 from enhancing transcriptional readthrough. In contrast, mutations of amino acids within this motif not predicted to coordinate zinc had no effect. Mutations of the predicted zinc coordinating residues in the $Cys_3$-$His_1$ motif also prevented M2-1 from interacting with the nucleocapsid protein. One mutation of a non-coordinating residue in the motif which did not affect readthrough during transcription, E10G, prevented interaction with the nucleocapsid protein. This suggests that M2-1 does not require interaction with the nucleocapsid protein in order to function during transcription. Analysis of the M2-1 protein in reducing SDS-PAGE revealed two major forms distinguished by their mobility. The slower migrating form was shown to be phosphorylated, whereas the faster migrating form was not. Mutations in the $Cys_3$-$His_1$ motif caused a change in distribution of the M2-1 protein from the slower to the faster migrating form. The data presented here show that the $Cys_3$-$His_1$ motif of M2-1 is essential for maintaining the functional integrity of the protein and are consistent with this motif coordinating the binding of zinc.

The present invention is drawn to a method of screening for antiviral compounds directed towards respiratory syncytial virus, comprising the steps of: a) treating a sample of respiratory syncytial virus with a compound, thereby producing a treated sample and an untreated sample; b) producing respiratory syncytial virus RNA transcripts in the presence of said treated sample or in the presence of said untreated sample; and c) comparing said transcripts produced in the presence of said treated sample with said transcripts produced in the presence of said untreated sample, wherein less readthrough transcripts due to termination at gene end signal produced in the presence of said treated sample is indicative of an antiviral compound directed towards respiratory syncytial virus. Representative samples of respiratory syncytial virus include a purified M2-1 protein, a M2-1 protein produced in cells from a vector, an isolated respiratory syncytial virus, a respiratory syncytial virus-infected cell or a respiratory syncytial virus-infected animal.

The present invention is also directed towards a method of screening for antiviral compounds directed towards respiratory syncytial virus, comprising the steps of: a) treating a sample of respiratory syncytial virus with a compound, thereby producing a treated sample and an untreated sample; and b) comparing the treated sample with an untreated sample, wherein an inhibitory effect on the treated sample compared to the untreated sample of a characteristic such as M2-1 transcriptional antitermination, zinc binding, phosphorylation, binding to respiratory syncytial virus N protein, viral transcription or generation of progeny virus particles is indicative of a compound with antiviral activity.

The present invention is also directed towards a method of screening for antiviral compounds directed towards respiratory syncytial virus, comprising the steps of: a) treating a sample of respiratory syncytial virus with a chelator or a compound that inhibits binding of Zinc; and b) comparing the treated sample with an untreated sample, wherein an inhibitory effect on the treated sample compared to the untreated sample of a characteristic such as M2-1 transcriptional antitermination, zinc binding, phosphorylation, binding to respiratory syncytial virus N protein, viral transcription or generation of progeny virus particles is indicative of a compound with antiviral activity. Preferably, the inhibition of zinc binding is the result of competing with zinc for binding to the Cys3-His1 motif, preventing zinc from binding, destroying the formation of the Cys3-His1 motif, or interfering with the interaction of the properly formed Cys3-His1 motif with its interacting target.

The present invention is also directed towards a method of screening for antiviral compounds directed towards respiratory syncytial virus, comprising the steps of: a) treating a sample of respiratory syncytial virus selected from the group consisting of core polymerase protein, nucleocapsid protein, phosphoprotein, an isolated virus or a virus-infected cell with a compound, thereby producing a treated sample and an untreated sample; and b) producing respiratory syncytial virus RNA transcripts in the presence of said treated sample or in the presence of said untreated sample, wherein an inhibition of virus RNA transcription or production of progeny virus particles in the presence of said treated sample is indicative of an antiviral compound directed towards respiratory syncytial virus.

The present invention is further directed towards a method of designing antiviral compounds directed towards respiratory syncytial virus, comprising the steps of: a) designing a compound that inhibits zinc binding to a $Cys_3$-$His_1$ motif of a respiratory syncytial virus M2-1 protein; b) treating a sample of respiratory syncytial virus with said designed compound; and c) comparing said treated sample with said untreated sample, wherein an inhibitory effect on said treated sample, when compared to the untreated sample, of a characteristic such as M2-1 transcriptional antitermination, zinc binding, phosphorylation, binding to respiratory syncytial virus N protein, viral transcription or generation of progeny virus particles is indicative of a compound with antiviral activity. Preferably, the inhibition of zinc binding is the result of competing with zinc for binding to the $Cys_3$-$His_1$ motif, preventing zinc from binding, destroying the formation of the $Cys_3$-$His_1$ motif, or interfering with the interaction of the properly formed $Cys_3$-$His_1$ motif with its interacting target. A preferred method of designing is by computer modeling.

As used herein, the term "antiviral compound" refers to any substance which inhibits the replication of a virus or inhibits any essential process in the replication cycle.

As used herein, the term "transcriptional antitermination" refers to the function of the M2-1 protein as a transcription factor which increases polymerase processivity and it enhances readthrough of intergenic junctions during RS virus transcription thereby acting as a transcription antiterminator.

As used herein, the term "zinc binding" refers to the tetrahedral coordination of a zinc ion within a protein by the 'R' groups of cysteine and histidine residues.

As used herein, the term "phosphorylation" refers to the addition of at least one phosphate group to the M2-1 protein via a covalent bond.

As used herein, "binding to respiratory syncytial virus N protein" refers to the interaction of the M2-1 protein with the respiratory syncytial virus N protein to generate a stable association of the N protein with the M2-1 protein (i.e. a complex of M2-1 and N).

The following examples are given for the purpose of illustrating various embodiments of the invention and are not meant to limit the present invention in any fashion:

EXAMPLE 1
cDNA Constructs

Vectors for expressing the M2-1 protein in eukaryotic cells were generated using a vaccinia T7 expression system. Generation of cDNAs expressing N, P, L, and wild-type M2-1 proteins (pN, pP, pL, and pORF1, respectively) has been described previously (13, 38). Mutations in the $Cys_3$-$His_1$ motif of the M2-1 protein were generated by PCR mutagenesis utilizing primers containing coding changes, and cloned into the BamHI/HindIII sites of pGEM3 behind the T7 promoter. Nucleotide sequences of cDNA constructs were determined by dideoxy nucleotide chain termination DNA sequencing. The generation of pM/SH (encoding an RS virus dicistronic subgenomic replicon) was described previously (13).

EXAMPLE 2
Virus and Cells

HEp-2 cells were grown in minimum essential medium (MEM) (GIBCO laboratories) supplemented with 5% heat-inactivated fetal bovine serum (FBS) in 60-mm dishes. The A-2 strain of human RS virus was propagated in HEp-2 cells. RS virus was added to the cells at a m.o.i. of 1 p.f.u./cell. Virus was allowed to adsorb for 2 h at 37° C. Fresh medium (2 mls of MEM supplemented with 5% FBS) was added, and cells were incubated at 37° C. for 18 h. The medium was removed, and medium deficient in methionine and cysteine or phosphate as required was added for 30 min. Proteins were labeled for 2 h using 66 uCi/ml [$^{35}$S]-methionine and cysteine (Tran$^{35}$S-label, ICN) or 100 uCi/ml [$^{33}$P]-inorganic phosphate (ICN). Cells were harvested, and cytoplasmic extracts were prepared as previously described (35). RS virus specific proteins were detected by immunoprecipitation followed by SDS-PAGE.

EXAMPLE 3
cDNA Transfections

RS virus RNA synthesis, programmed by subgenomic replicons, was assayed using a recombinant vaccinia virus T7 expression system. HEp-2 cells infected with recombinant MVA vaccinia virus expressing T7 RNA polymerase were transfected with 6 ug of pM/SH, 5 ug of pN, 2 ug of pP, 2 ug of pL, and 0.3 ug pORF1 (encoding wild-type M2-1 protein) or pGEM-based plasmid encoding mutant M2 protein. RS virus-specific RNAs were labeled with [$^3$H] uridine (33 uCi/ml; Moravek) in the presence of actinomycin D (10 ug/ml; Sigma) and cytosine arabinoside (50 ug/ml; Sigma) at 16 h post-transfection. After a 5-h labeling period, cells were harvested and cytoplasmic extracts were prepared as previously described (26). RNAs were purified by phenol extraction followed by ethanol precipitation. RNAs were analyzed by electrophoresis in 1.75% agarose-urea gels and detected by fluorography (19, 34).

Expression of M2-1 mutant proteins was analyzed by transfecting vTF7-3-infected HEp-2 cells with 2 ug of pGEM-based plasmids encoding the wild-type M2-1 protein or mutant M2-1 proteins. The interaction of the M2-1 protein with the nucleocapsid protein was analyzed in cells cotransfected with the M2-1 plasmids encoding wild-type or mutant M2-1 proteins and 5 ug pN. Sixteen-hours post-transfection cells were incubated in methionine/cysteine-free medium or phosphate-free medium (ICN) for 30 min and then exposed to [$^{35}$S]-methionine and cysteine (66 uCi/ml; Tran$^{35}$S-label, ICN) or [$^{33}$P]-inorganic phosphate (100 uCi/ml; ICN). Following a 2-h labeling period, cells were harvested and cytoplasmic extracts were prepared as previously described.

EXAMPLE 4
Pulse-chase analysis of M2-1 protein

M2-1 protein maturation and stability were analyzed by metabolic labeling with a short exposure to [$^{35}$S]-methionine and cysteine (pulse) followed by varying incubation times post-label (chase). HEp-2 cells infected with vTF7-3 were transfected with plasmid encoding the wild-type M2-1 protein as described above. Sixteen-hour post-transfection cells were incubated in methionine/cysteine free medium for 30 min and then exposed to [$^{35}$S]-methionine and cysteine (100 uCi/ml; Tran$^{35}$S-label, ICN) for 15 min. Following the labeling period, cells were either harvested and cytoplasmic extracts prepared, or the label was removed, cells were washed and fresh medium containing excess unlabeled methionine and cysteine (10 mM) was added for 15-, 30-, or 60-min prior to harvest.

EXAMPLE 5
Immunoprecipitations of Labeled Proteins

Immunoprecipitation of RS virus-specific proteins from cytoplasmic extracts was performed using an M2-1 protein-specific monoclonal antibody (MAb), 5H5 or 1C13 (the kind gift from G Toms), or a polyclonal anti-RS virus serum (Chemicon International) and protein-G Sepharose (Pharmacia Biotech). Immunoprecipitated proteins were analyzed by SDS-PAGE in 11% polyacrylamide gels under reducing conditions and detected by fluorography (2, 17).

Figure 1A:
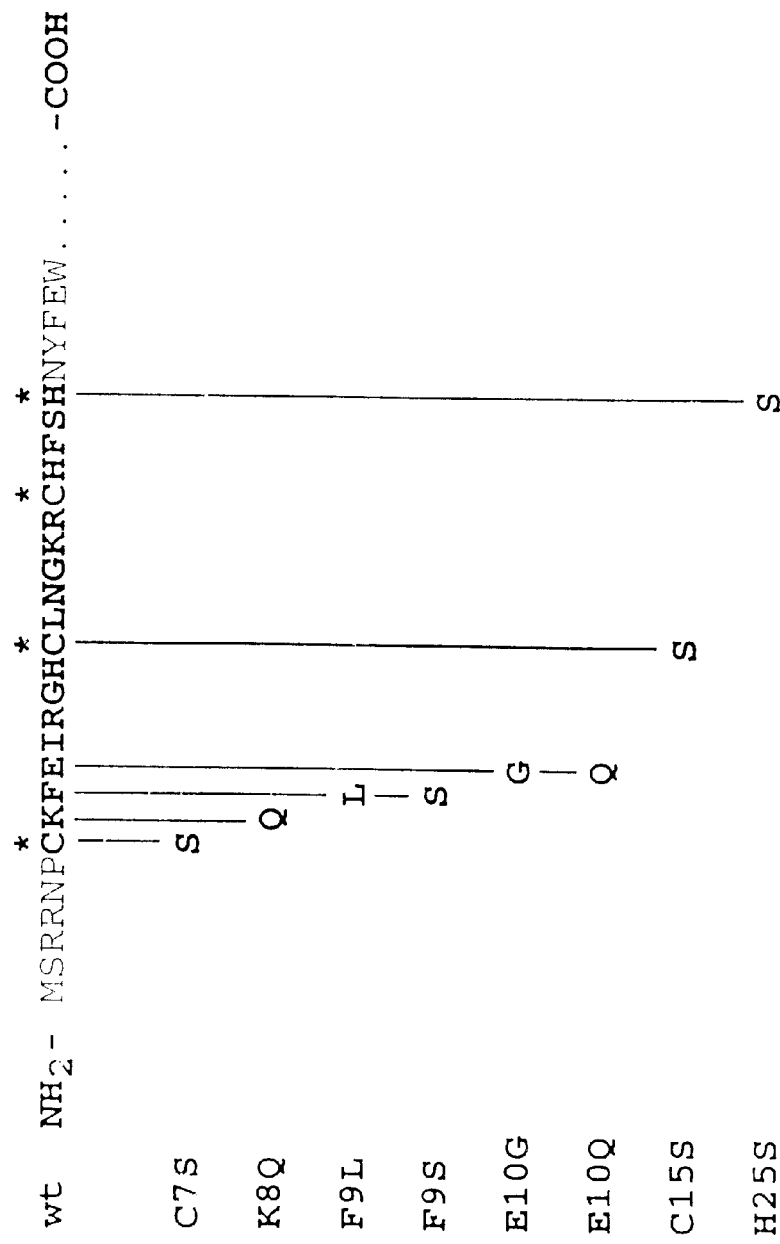
FIG. 1A shows a diagram of the mutations made in the $Cys_3$-$His_1$ motif. $NH_2$ signifies the amino terminus of the M2-1 protein. The predicted zinc coordinating residues are identified by an asterisk.

EXAMPLE 6
Effect of Mutations in the $Cys_3$-$His_1$ Motif of M2-1 Protein on RS Virus Transcription The M2-1 protein causes a decrease in the efficiency of transcription termination at RS virus gene junctions resulting in an increased production of readthrough transcripts, thus functioning as a transcription antiterminator (8, 13). Sequence analysis revealed that the M2-1 protein contains a $Cys_3$-$His_1$ amino acid sequence motif (C—$X_7$—C—$X_5$—C—$X_3$—H). A similar motif has been shown to bind zinc in Nup475 protein, a mammalian transcription factor (36). To determine whether this motif was important for the M2-1 protein to function as an antiterminator during viral transcription, point mutations were generated in the cDNA encoding the M2-1 protein (FIG. 1A). Three of the residues predicted to coordinate a zinc ion, the cysteine residues at positions 7 and 15, and the histidine at position 25, were each changed to serines. The mutants were named according to the following terminology: C7S, C15S and H25S. In addition three other residues within the motif which would not be predicted to be involved in coordinating a zinc ion were mutated as controls: K8Q, F9L, F9S, E10G and E10Q (FIG. 1A). The mutant M2-1 ORFs were cloned behind the T7 promoter in pGEM3.

Figure 1B:
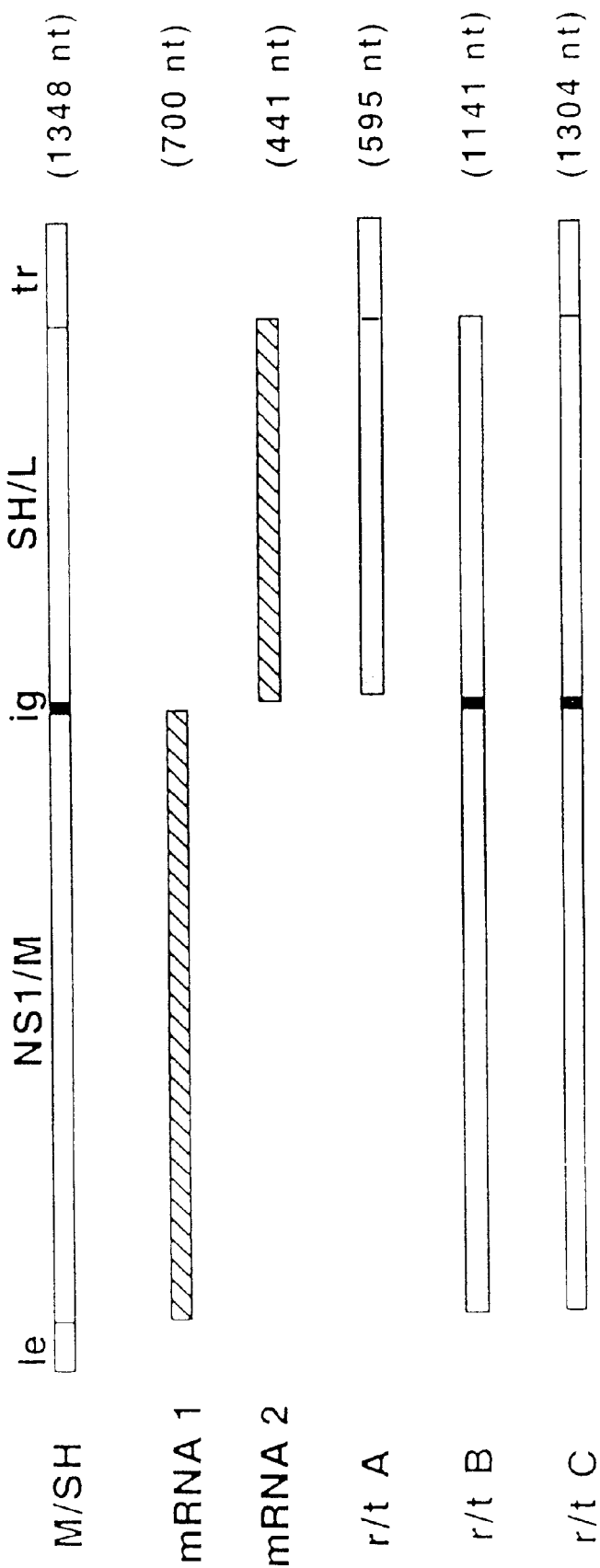
FIG. 1B shows a diagram of the RS virus dicistronic subgenomic replicon containing the M/SH intergenic junction used in the transcription assay and the potential products of transcription.
Figure 1C:
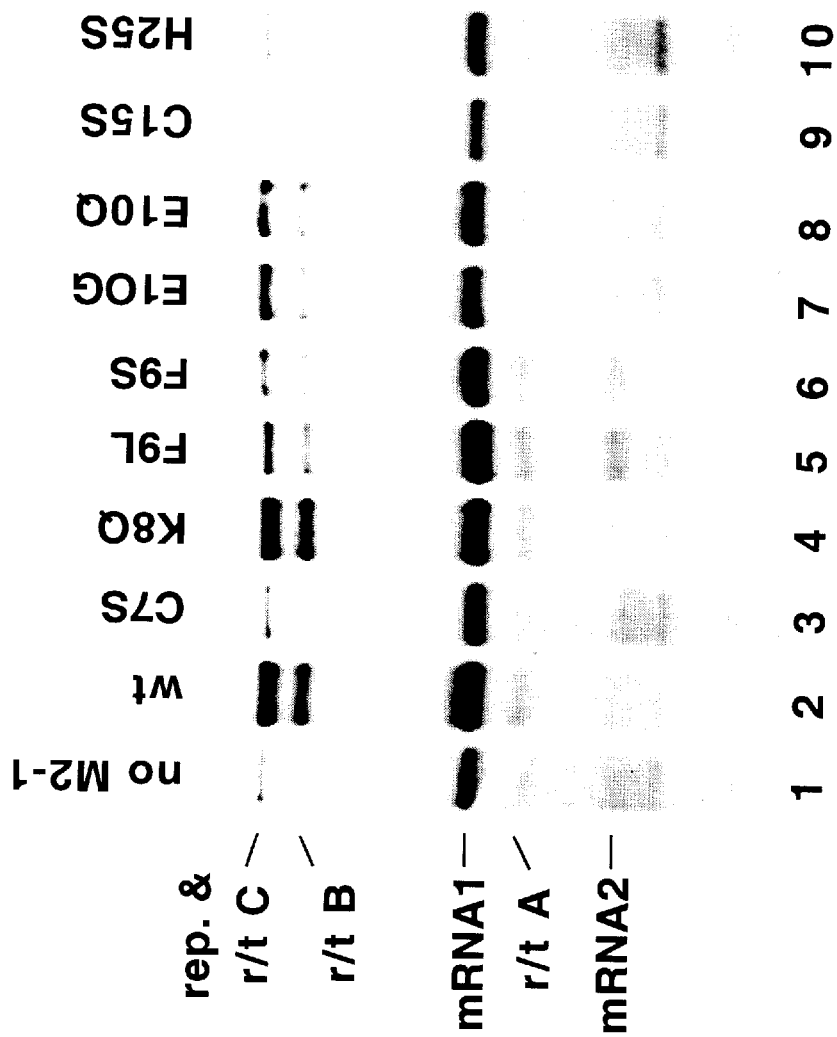
FIG. 1C shows the products of RNA synthesis from the M/SH subgenomic replicon in the presence of wild-type (wt) or mutated M2-1 proteins. Cells infected with recombinant MVA vaccinia virus expressing T7 RNA polymerase, were transfected with pM/SH, pN, pP, pL, and plasmids expressing wild type or mutant M2-1 proteins as indicated. Cells were exposed to [$^3$H]-uridine in the presence of actinomycin-D and cytosine arabinoside. Total RNA was phenol extracted, ethanol precipitated and analyzed by agarose-urea gel electrophoresis followed by fluorography. rep, replication products; r/t, products of readthrough transcription.

The effects of mutations in the $Cys_3$-$His_1$ motif of the M2-1 protein on RS virus transcription were assayed using an RS virus subgenomic replicon supported by the recombinant vaccinia virus-T7 expression system (38). An RS virus subgenomic replicon containing two genes separated by the M/SH gene junction (FIG. 1B) was expressed from cDNA in cells also expressing the N, P, L and M2-1 proteins from T7 expression plasmids. The construction of this subgenomic replicon has been described previously (13). The effect of the wild type and mutant M2-1 proteins on RS virus transcription was determined by direct metabolic labeling of RNA. The synthesis of discrete monocistronic mRNA1 and mRNA2 (FIG. 1B) was analyzed in comparison to the synthesis of the dicistronic mRNA, r/t B, generated by the failure of the polymerase to terminate transcription at the end of mRNA1. The wild-type M2-1 protein decreased transcriptional termination and increased readthrough transcription as previously reported (11, 13). The increase in readthrough transcription can be seen by comparing lanes 1 and 2 of FIG. 1C. In the absence of M2-1, primarily the products of replication and mRNA1, mRNA2, and a small amount of readthrough from mRNA2 into trailer (r/t A) were synthesized. In the presence of M2-1, a significant increase in the products of readthrough transcription (polycistronic mRNAs) occurred, shown most strikingly by the presence of r/t B (a dicistronic mRNA consisting of the sequences of mRNA1 and mRNA2). Detailed identification of the RNAs in FIG. 1C has been presented in previous work (13). The data in FIG. 1C show that the M2 proteins in which residues which are not predicted to coordinate the binding of a zinc ion were changed (K8Q, F9L, F9S, E10G, and E10Q) functioned similar to the wt M2-1 protein in causing an increase in readthrough transcription (FIG. 1C, lanes 2, 4, 5, 6, 7, and 8). However, mutations of the residues of M2-1 which are predicted to coordinate the binding of a zinc ion inhibited the ability of the protein from increasing readthrough transcription (FIG. 1C, lanes 3, 9, and 10). Thus, the integrity of the $Cys_3$-$His_1$ motif was important for maintaining the function of the M2-1 protein as an antiterminator during RS virus transcription.

Figure 2:
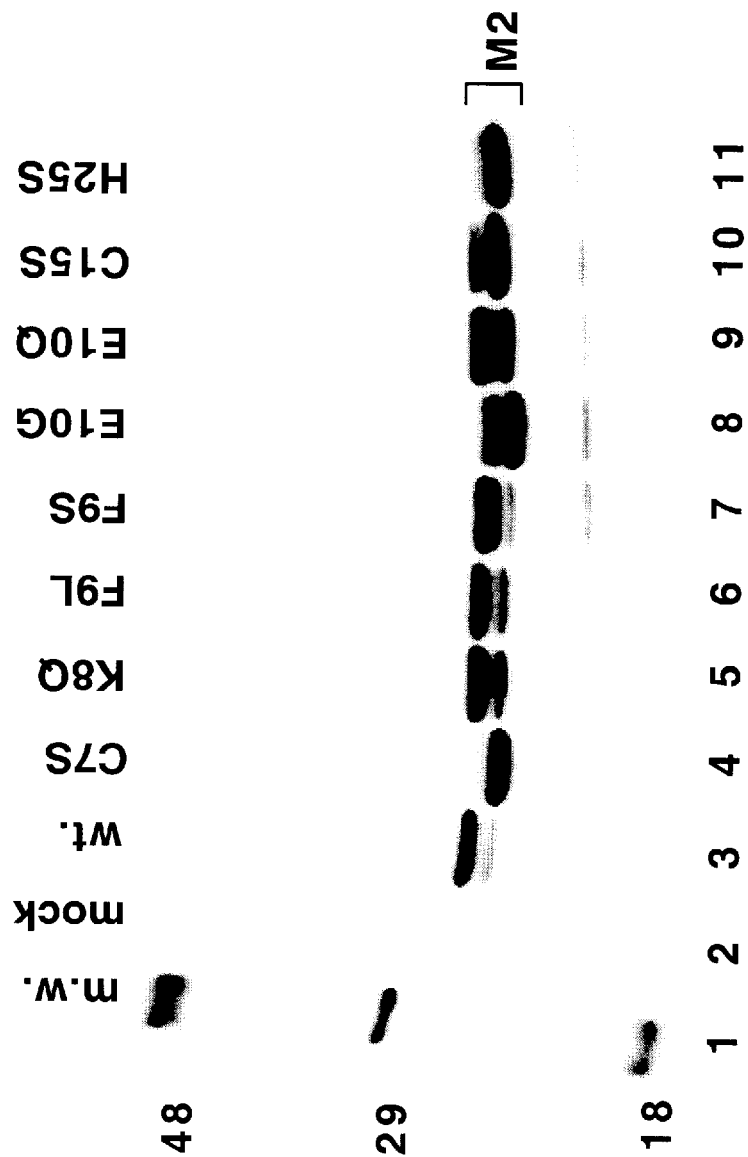
FIG. 2 shows the expression of M2-1 proteins with mutations in the $Cys_3$-$His_1$ motif. HEp-2 cells were infected with vTF7-3 and then transfected with plasmids encoding the wild type or mutant M2-1 proteins. Cells were labeled with [$^{35}$S]-methionine and cysteine for 2 h at 16 h post-transfection. Cytoplasmic extracts were prepared and proteins were immunoprecipitated with the M2-specific MAb, 5H5. Labeled proteins from mock-transfected cells (lane 2) and cells transfected with plasmids encoding the M2-1 proteins (lanes 3 to 11) were analyzed by SDS-PAGE in 11% polyacrylamide gels, followed by fluorography. Lane 1, [$^{14}$C]-labeled molecular size markers; molecular sizes in kilodaltons are shown on the left of the gel. Position of the M2-1 protein(s) is indicated. wt, wild type.

EXAMPLE 7
Effects of Mutations in the $Cys_3$-$His_1$ Motif on M2-1 Protein Mobility in SDS-PAGE Expression of each of the mutant M2-1 proteins was analyzed by immunoprecipitation followed by reducing SDS PAGE to test whether each of the mutant proteins was expressed and stable. We also examined the effects of the mutations on electrophoretic mobility as previous reports showed the M2 protein migrated as a doublet (27). The wild type and mutant M2-1 proteins were expressed in HEp-2 cells from cDNAs using the recombinant vaccinia virus T7 expression system. Proteins were labeled with [$^{35}$S]-methionine and cysteine and immunoprecipitated from cell lysates using an M2-specific MAb, 5H5. Immunoprecipitated proteins were analyzed by SDS-PAGE under reducing conditions. In FIG. 2, it can be seen that specific mutations affected the mobility of the M2 protein. The wild-type protein migrated as a doublet, with the majority of the protein present as the slower migrating form (FIG. 2, lane 3). This was also true of K8Q, F9L, F9S and E10Q (FIG. 2, lanes 5, 6, 7 and 9). The mutation E10G caused a shift in the distribution of protein from the slower to the faster migrating form and a slight increase in mobility (FIG. 2, lane 8). Mutations of the residues predicted to coordinate the binding of zinc (C7S, C15S, and H25S) caused a significant shift from the slower to the faster migrating form of the protein (FIG. 2, lanes 4, 10, and 11). Thus, mutations in this region had a significant effect on the electrophoretic mobility of the M2-1 protein specifically altering the distribution of protein between a slower and faster migrating form.

Figure 3:
FIG. 3 shows a pulse-chase analysis of wild-type M2-1 protein expression. HEp-2 cells infected with vTF7-3 were transfected with a plasmid expressing the wild-type M2-1 protein. Cells were exposed to [$^{35}$S]-methionine and cysteine for 15-min. at 16-h post-transfection. Following the 15-min. labeling period, cells were either harvested (lanes 1 and 2), or the medium was removed and medium containing unlabeled methionine and cysteine was added for 15 min. (lane 3), 30 min. (lane 4), or 60 min. (lane 5) prior to harvest. Labeled proteins were immunoprecipitated from cytoplasmic extracts using M2-1 specific MAb 1C13. Immunoprecipitated proteins were analyzed by SDS-PAGE under reducing conditions in 11% polyacrylamide gels followed by fluorography. vv, mock transfection.

The nature of the two forms of the M2 protein, seen as a doublet in reducing SDS-PAGE was investigated by metabolic pulse labeling with [$^{35}$S]-methionine and cysteine, followed by a chase with excess unlabeled amino acids. The faster migrating form of M2-1 was labeled initially (FIG. 3, lane 2) and then over time chased into the slower migrating form (FIG. 3, lanes 3, 4 and 5). These results suggest that the slower migrating form was a post-translationally modified form of the M2-1 protein (FIG. 3).

EXAMPLE 8
Phosphorylation of M2-1 Protein

The M2-1 protein has previously been reported to be phosphorylated in RS virus-infected cells (18). Results of the above pulse-chase analysis (FIG. 3) suggested that the cause of the difference in mobility of the two forms of M2-1 was due to a post-translational modification. Therefore, studies were performed to investigate whether the mobility differences of the M2-1 protein in SDS-Page was related to its phosphorylation state. Wild-type M2-1 and mutant M2-1 proteins, C7S and E10G, were expressed in vTF7-3 infected cells and labeled with [$^{35}$S]-methionine and cysteine, or with [$^{33}$P]-inorganic phosphate. Proteins synthesized in RS virus-infected cells were labeled under the same conditions. Labeled proteins were immunoprecipitated with MAb 5H5 or polyclonal antiserum to RS virus and analyzed by SDS-PAGE under reducing conditions.

Figure 4:
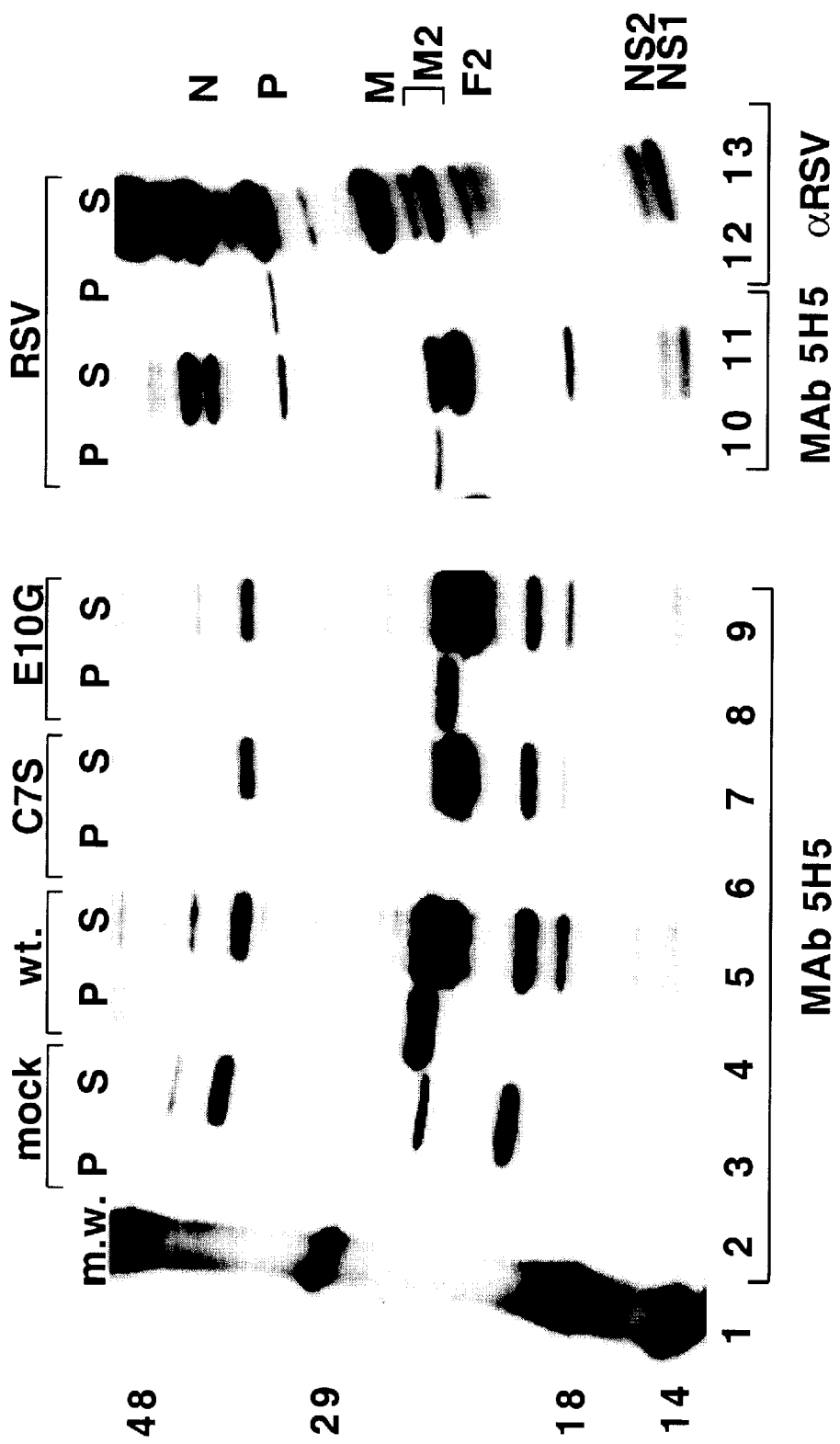
FIG. 4 shows the effects of mutations in the $Cys_3$-$His_1$ motif of the M2-1 on phosphorylation. HEp-2 cells infected with vTF7-3 were mock-transfected (mock; lanes 2 and 3) or transfected with plasmid encoding wild type or mutant M2-1 proteins as indicated (lanes 4 to 9), or HEp-2 cells infected with RS virus (RSV; lanes 10 to 13). Cells were exposed to [$^{35}$S]-methionine and cysteine (S; lanes 3, 5, 7, 9, 11, and 13) or [$^{33}$P]-inorganic phosphate (P; lanes 2, 4, 6, 8, 10, and 12) for 2 h at 16 h post-transfection or 20 h post-infection. Labeled proteins were immunoprecipitated using M2-1 specific MAb 5H5 (lanes 2 to 11), or anti-RS virus polyclonal serum (aRSV; lanes 12 and 13) and analyzed by SDS-PAGE in 11% polyacrylamide gels followed by fluorography. Positions of RS virus proteins are shown (lane 13). The exposure time of lanes 10 to 13 was two times that of lanes 1 to 9. m.w., molecular size markers, size in kilodaltons. wt, wild type.

Analysis of the [$^{35}$S]-labeled M2-1 protein produced in RS virus-infected cells showed it was present as a doublet with the majority of the protein (approximately 75%) found in the faster migrating form (FIG. 4, lanes 11 and 13). When labeled with [$^{33}$P]-inorganic phosphate, only a single labeled band was observed which corresponded to the slower migrating form of M2-1 (FIG. 4, lanes 10 and 12). Expression of the wild-type M2-1 protein alone from a plasmid in cells also showed that it was the slower form of M2-1 that was phosphorylated, whereas the faster form was not (FIG. 4, lanes 4 and 5). This demonstrated that the M2-1 protein could be phosphorylated in the absence of other RS virus proteins. In contrast, the majority of the mutant C7S M2-1 protein migrated as the faster form which was not detectably phosphorylated (FIG. 4, lanes 6 and 7). Analysis of the E10G M2-1 mutant protein showed a shift in the distribution towards the faster migrating form which corresponded with an approximately 50% decrease in phosphorylation compared to wt M2-1 protein (FIG. 4, lanes 8 and 9).

These results showed that the faster and slower migrating forms of M2-1 protein observed by SDS-PAGE under reducing conditions were differentiated by their phosphorylation state; the slower migrating form was phosphorylated and the faster migrating form was not. In addition, the mutations of the predicted zinc coordinating residues in the $Cys_3$-$His_1$ motif prevented efficient phosphorylation of the M2-1 protein. Treatment of the wild type M2-1 protein with calf alkaline phosphatase (CIP) confirmed these results as digestion with CIP resulted in a shift of the slower migrating form to the faster form (T. Cartee, unpublished data).

Figure 5:
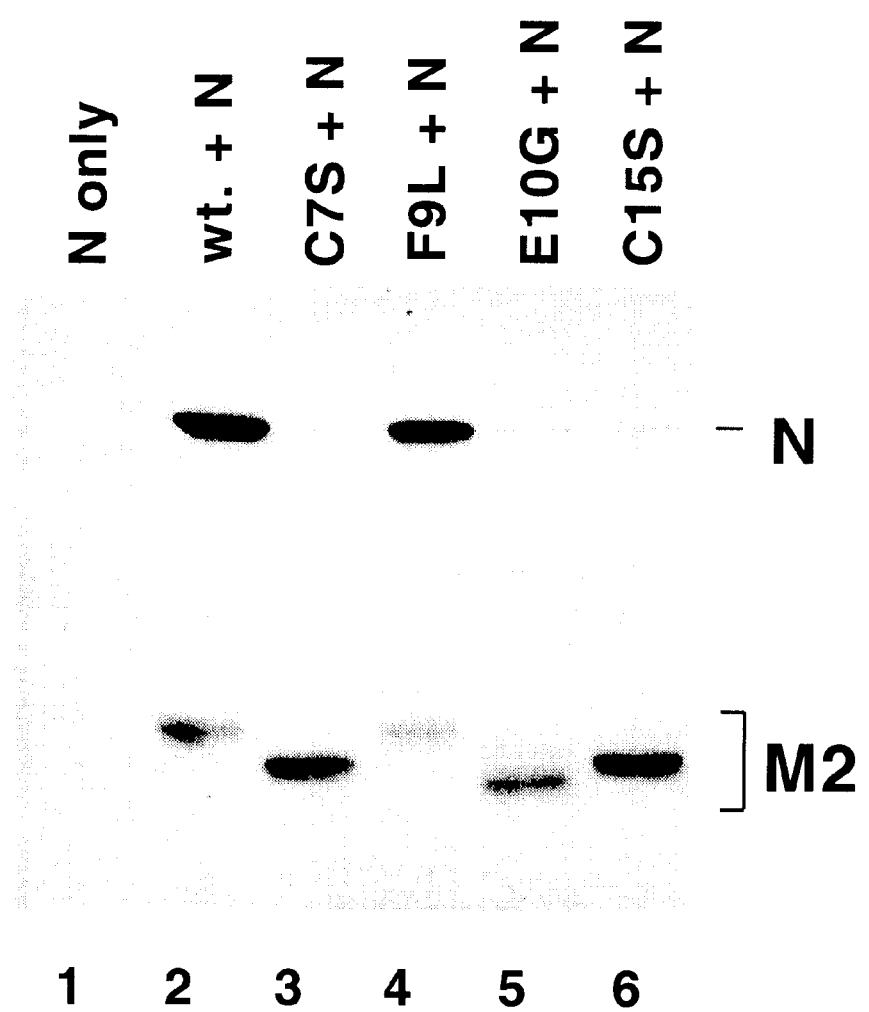
FIG. 5 shows the effects of mutations in the $Cys_3$-$His_1$ motif of the M2-1 protein on interaction with the N protein.

EXAMPLE 9
Effects of Mutations in $Cys_3$-$His_1$ Motif of M2-1 on the Interaction with N Protein The M2-1 and N proteins have been demonstrated to interact in RS virus infected cells and when the two proteins are co-expressed (9). The effect of mutations in the $Cys_3$-$His_1$ motif of the M2-1 protein on its interaction with the N protein was assayed by coexpression of wild type and mutant M2-1 proteins with the N protein in HEp-2 cells. Proteins labeled with [$^{35}$S]-methionine and cysteine were immunoprecipitated from cell lysates using the M2-1 specific MAb, 5H5, and analyzed by SDS-PAGE under reducing conditions. The N protein was coprecipitated with the wild-type and F9L M2-1 proteins (FIG. 5, lanes 2 and 4). Mutation of the cysteine residues at positions 7 and 15 (FIG. 5, lanes 3 and 6) and the histidine at position 25 (data not shown) of the M2-1 protein severely decreased the efficiency with which N protein was coprecipitated, demonstrating the importance of the predicted zinc-coordinating residues for maintenance of the M2-1 interaction with N protein. Surprisingly, the E10G mutation, which did not prevent M2-1 protein mediated antitermination during RS virus transcription, prevented the M2-1 protein from interacting with the N protein. The reason for this is not clear, but may be related to the presence of a glycine residue rather than the loss of the glutamate as the E10Q mutation in the M2-1 protein did interact with the N protein (data not shown).

These results demonstrate the requirement for maintaining the $Cys_3$-$His_1$ motif in order for M2-1 protein to interact with N protein. In addition, the phenotype of the E10G mutation suggested that the interaction is specific in that it can be disrupted by a single mutation in a non-coordinating residue of the predicted zinc-binding domain. This mutation separates the function of M2-1 protein in transcription from its ability to interact with N protein, implying that this interaction is not required for M2 to function during transcription. However, the conditions under which the immunoprecipitations were performed were stringent and may disrupt weak interactions which could be functionally relevant in cells. Additionally it should be noted that these results do not rule out the possibility that this interaction is mediated via another molecule with which both N and M2-1 proteins interact.

EXAMPLE 10
Requirement of Individual RS Virus Protein for RNA Transcription and Replication The requirement for individual RS virus proteins in order to obtain RNA transcription and replication was examined. Cells were infected with VVT7 and transfected with plasmids expressing a subgenomic RS virus RNA replicon, pWT5 (FIG. 6), and, in various combinations, individual plasmids expressing the RS virus core polymerase protein (L), the nucleocapsid protein (N), the phosphoprotein (P) or M2-1 protein.

As can be seen in FIG. 7 lane 4, cells transfected with all 5 plasmids synthesized the genomic positive and negative strand RNA products of replication and the single mRNA product of transcription as well as a transcriptive product of readthrough from failing to terminate at the end of the mRNA and reading through into the trailer gene. Omission of the N, P or L expression plasmids individually (lanes 3, 5, or 1 respectively) resulted in failure of any RNAs to be synthesized. Omission of the M2-1 expression plasmid (lane 2) resulted in failure to synthesize the transcriptive readthrough RNA. Thus these data showed that the N, P and L genes are sufficient for RNA replication, but the M2-1 protein provides an additional function for transcription. It serves as a transcription antiterminator.

Discussion

Sequence analysis of the RS virus M2-1 protein revealed a $Cys_3$-$His_1$ motif which had been shown to bind zinc in another protein (5, 36). Mutational analysis of the $Cys_3$-$His_1$ motif demonstrated that maintaining the cysteine and histidine residues predicted to coordinate zinc was essential for the functional integrity of the M2-1 protein. Alteration of the predicted zinc-coordinating residues resulted in an M2-1 protein which was unable to enhance transcriptional readthrough at RS virus gene ends. In addition, mutations of the predicted zinc coordinating residues resulted in an alteration in the migration pattern of the M2-1 protein in SDS PAGE from a relatively slow to a relatively fast migrating form. The two forms of M2-1 protein differed in phosphorylation, the slower form being phosphorylated and the faster form not.

Mutation of the predicted zinc coordinating residues also inhibited the interaction of the M2-1 protein with the N protein. Mutating any one of the residues of the M2-1 protein predicted to coordinate zinc resulted in the same phenotype, whereas mutating other non-coordinating residues in the $Cys_3$-$His_1$ motif had little if any effect on the antitermination function of the M2-1 protein. Thus maintaining the potential zinc coordinating residues of the $Cys_3$-$His_1$ motif was essential for M2-1 function. These results are consistent with the idea that the $Cys_3$-$His_1$ motif coordinates the binding of an ion of zinc. Studies are underway to directly demonstrate that M2-1 binds zinc using various techniques.

The data presented here show that the two forms of M2-1 protein separated by SDS-PAGE under reducing conditions are discriminated by whether or not they are phosphorylated. The slower migrating form of M2-1 was phosphorylated, whereas the faster form was not. Multiple forms of the M2-1 protein can be seen in FIGS. 2 and 3, two major bands and at least two other minor species. These minor species may correspond to those observed by Routledge et al. in infected cells (27). Additionally, the extent to which the M2-1 protein is phosphorylated has not yet been determined and the less prevalent species may represent differentially phosphorylated forms of M2-1.

The integrity of the $Cys_3$-$His_1$ motif was important for phosphorylation. Protein folding studies have shown that zinc binding and protein folding are tightly coupled with zinc binding conferring structural stability (6). One could hypothesize that M2-1 which has zinc bound is folded and can be recognized by the appropriate cellular kinase, whereas mutants which prevent the binding of zinc would not be properly folded and would not be recognized by the kinase. Such a model would mean that zinc binding is essential for phosphorylation, which, in turn, may play a role in M2-1 function. In such a scenario, zinc binding could play a crucial role in the regulation of RS virus transcription.

The role of the M2-1:N protein-protein interaction in the RS virus replication cycle is currently unknown. The E10G M2-1 protein is active in transcription, but results reported above indicate that it does not interact with the N protein, suggesting that this interaction is not required for M2-1 to enhance transcriptional readthrough. This interaction may be important at another point during virus replication. The M2-1 protein was initially characterized as a matrix-like protein as it dissociated from nucleocapsids under similar conditions to the matrix protein, M (14). If M2-1 can function as a matrix like protein, in addition to its activity during transcription, it is possible that the interaction between M2-1 and N may be involved in virus assembly.

Zinc-binding motifs have been found in a number of proteins and, in many cases, mediate protein-protein or protein-nucleic acid interactions (1, 21, 22, 23, 30, 31, 32). Often the binding of zinc plays a purely structural role holding the protein in a conformation which is functional (24). It is hypothesized that the $Cys_3$-$His_1$ motif of M2-1 binds zinc in order for the protein to be in a conformation which allows it to function in RS virus transcription, to interact with the N protein, and to be efficiently phosphorylated. In conclusion, the data presented above demonstrated that the predicted zinc-binding motif of M2-1 is essential for maintaining the functional integrity of the protein, and that there are at least two forms of M2-1 produced in infected cells which can be distinguished by their phosphorylation state.

The following references were cited herein:
1. Bowles, N. E. 1993. Effect of rearrangements and duplications of the cys-his motifs of Rous sarcoma virus nucleocapsid protein. J. Virol. 67:623–631.
2. Chamberlain, J. P. 1979. Fluorographic detection of radioactivity in polyacrylamide gels with water soluble fluor, sodium salicylate. Anal. Biochem. 98:132–135.
3. Collins, P. L., M. G. Hill, J. Cristina, and H. Grosfeld. 1996. Transcription elongation factor of respiratory syncytial virus, a non-segmented negative-strand RNA virus. Proc. Natl. Acad. Sci. USA 93:81–85.
4. Collins, P. L., Y. T. Huang, and G. W. Wertz. 1984. Identification of a tenth mRNA of respiratory syncytial virus and assignment of polypeptides to the 10 viral genes. J. Virol. 49:572–578.
5. Collins, P. L., and G. W. Wertz. 1985. The envelope-associated 22K protein of human respiratory syncytial virus: Nucleotide sequence of the mRNA and a related polytranscript. J. Virol. 54:65–71.
6. Eis, P. S., and J. R. Lakowicz. 1993. Time-resolved energy transfer measurements of donor-acceptor distance distributions and intramolecular flexibility of a CCHH zinc-finger peptide. Biochemistry 32:7981–7993.
7. Emerson, S. U., and R. R. Wagner. 1972. Dissociation and reconstitution of the transcriptase and template activities of vesicular stomatitis B and T virions. J. Virol. 10:297–309.
8. Fearns, R., and P. L. Collins. 1999. Role of the M2-1 transcription antitermination protein of respiratory syncytial virus in sequential transcription. J. Virol. 73:5852–64.
9. Garcia, J., B. Garcia-Barreno, A. Vivo, and J. Melero. 1993. Cytoplasmic inclusions of respiratory syncytial virus-infected cells: formation of inclusion bodies in transfected cells that co-express the nucleoprotein, the phosphoprotein, and the 22K protein. Virology 195:243–247.
10. Grosfeld, H., M. Hill, and P. L. Collins. 1995. RNA replication by respiratory syncytial virus (RSV) is directed by the N, P, and L proteins; transcription also occurs under these conditions but requires RSV superinfection for efficient synthesis of full-length mRNA. J. Virol. 69:5677–5686.
11. Hardy, R. W., S. B. Harmon, and G. W. Wertz. 1999. The diverse gene junctions of respiratory syncytial virus modulate the efficiency of transcription termination and respond differently to M2-mediated antitermination. Journal of Virology 73:170–176.
12. Hardy, R. W., and G. W. Wertz. unpublished data.
13. Hardy, R. W., and G. W. Wertz. 1998. The product of the respiratory syncytial virus M2 gene ORF1 enhances readthrough of intergenic junctions during viral transcription. J. Virol. 72:520–526.
14. Huang, Y. T., P. L. Collins, and G. W. Wertz. 1985. Characterization of the 10 proteins of human respiratory syncytial virus: identification of a fourth envelope associated protein. Virus Res. 2:157–173.
15. Huang, Y. T., and G. W. Wertz. 1982. The genome of respiratory syncytial virus is a negative stranded RNA that codes for at least seven mRNA species. J. Virol. 43:150–157.
16. Keilin, D., and T. Mann. 1940. Carbonic anhydrase. Purification and nature of the enzyme. Biochem. J. 34:1163–1176.
17. Laemmli, U. K. 1970. Cleavage of structural proteins during the assembly of the head of bacteriophage T4. Nature 227:680–685.
18. Lambert, D. M., J. Hambor, M. Diebold, and B. Galinski. 1988. Kinetics of synthesis and phosphorylation of respiratory syncytial virus polypeptides. J. Gen. Virol. 69:313–323.
19. Laskey, R. 1980. The use of intensifying screens or organic scintillators for visualizing radioactive molecules resolved by gel electrophoresis. Methods Enzymol. 65:363–371.
20. Ling, R., A. J. Easton, and C. R. Pringle. 1992. Sequence analysis of the 22K, SH and G genes of the turkey rhinotracheitis virus and their intergenic regions reveals a gene order different from that of other pneumoviruses. J. Gen. Virol. 73:1709–1715.
21. Mabrouk, T., and G. Lemay. 1994. Mutations in a CCHC zinc binding motif of the reovirus s3 protein decrease its intracellular stability. J. Virol. 68:5287–5290.
22. Meric, C., and S. P. Goff. 1989. Characterization of Moloney murine leukemia virus mutants with single amino acid substitutions in the cys-his box of the nucleocapsid protein. J. Virol. 63:1558–1568.
23. Meric, C., E. Gouilloud, and P.-F. Spahr. 1988. Mutations in Rous sarcoma virus nucleocapsid protein p12 (NC): Deletions of Cys-His boxes. J. Virol. 62:3328–3333.
24. Miller, J., A. D. McLachlan, and A. Klug. 1985. Repetitive zinc-binding domains in the protein transcription factor IIIA from Xenopus oocytes. EMBO J. 4:1609–1614.
25. Mink, M. A., D. S. Stec, and P. L. Collins. 1991. Nucleotide sequences of the 3' leader and 5' trailer regions of human respiratory syncytial virus genomic RNA. Virology 185:615–624.

26. Pattnaik, A. K., and G. W. Wertz. 1990. Replication and amplification of defective interfering particle RNAs of vesicular stomatitis virus in cells expressing viral proteins from vectors containing cloned cDNAs. J. Virol. 64:2948–2957.
27. Routledge, E. G., M. M. Willcocks, L. Morgan, A. C. R. Samson, R. Scott, and G. L. Toms. 1987. Heterogeneity of the respiratory syncytial virus 22K protein revealed by Western blotting with monoclonal antibodies. J. Gen. Virol. 68:1209–1215.
28. Samal, S. K., M. K. Pastey, T. H. McPhillips, and S. B. Mohanty. 1993. Bovine respiratory syncytial virus nucleocapsid protein expressed in insect cells specifically interacts with the phosphoprotein and the M2 protein. Virology 193:470–473.
29. Sanchez, A., M. P. Kiley, B. P. Holloway, and D. D. Auperin. 1993. Sequence analysis of the Ebola virus genome: organization, genetic elements, and comparison with the genome of Marburg virus. Virus Res. 29:215–240.
30. Sands, M. S., and D. F. Bogenhagen. 1991. Two zinc-finger proteins from Xenopus laevisbind the same region of 5S RNA but with different nuclease protection patterns. Nucleic Acid Res. 19:1797–1803.
31. Shepard, D. A., J. G. Ehnstrom, P. J. Skinner, and L. A. Schiff. 1996. Mutations in the zinc-binding motif of the reovirus capsid protein s3 eliminates its ability to associate with capsid protein ml., J. Virol. 70:2065–2068.
32. Somers, W., M. Ultsch, A. De Vos, and A. A. Kossiakoff. 1994. The X-ray structure of a growth hormone-prolactin complex. Nature 372:478–481.
33. Stec, D. S., M. G. Hill, and P. L. Collins. 1991. Sequence analysis of the polymerase L gene of human respiratory syncytial virus and predicted phylogeny of nonsegmented negative strand viruses. Virology 183:273–287.
34. Wertz, G. W., and N. L. Davis. 1981. Characterization and mapping of RNaseIII cleavage sites in vesicular stomatitis virus genome RNA. Nucleic Acids Res. 9:6487–6503.
35. Wertz, G. W., M. Kreiger, and L. A. Ball. 1989. Structure and cell surface maturation of the attachment glycoprotein of human respiratory syncytial virus from recombinant vaccinia virus in a cell line deficient in O-glycosylation. J. Virol. 71:1794–1801.
36. Worthington, M. T., B. T. Amann, D. Nathans, and J. M. Berg. 1996. Metal binding properties and secondary structure of the zinc binding domain of Nup475. Proc. Natl. Acad. Sci. USA 93:13754–13759.
37. Yu, Q., P. J. Davis, T. D. K. Brown, and D. Cavanagh. 1992. Sequence and in vitro expression of the M2 gene of turkey rhinotracheitis pneumovirus. J. Gen. Virol. 73:1355–1363.
38. Yu, Q., R. W. Hardy, and G. W. Wertz. 1995. Functional cDNA clones of the human respiratory syncytial (RS) virus N, P, and L proteins support replication of RS virus genomic RNA analogs and define the minimal trans-acting requirements for RNA replication. J. Virol. 69:2412–2419.
39. Zamora, M., and S. K. Samal. 1992. Sequence analysis of M2 mRNA of bovine respiratory syncytial virus obtained from an F-M2 dicistronic mRNA suggests structural homology with that of human respiratory syncytial virus. J. Gen. Virol. 73:737–741.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of screening for potential antiviral compounds directed against respiratory syncytial virus (RSV), comprising the steps of:
   a) treating a sample comprising RSV M2-1 protein with a compound; and
   b) comparing an activity of M2-1 protein with the activity in an untreated sample, said M2-1 protein activity is selected from the group consisting of zinc binding of M2-1 protein, phosphorylation of M2-1 protein and M2-1 protein binding to respiratory syncytial virus N protein, wherein a decreased activity in the treated sample indicates said compound is potentially an antiviral compound directed against respiratory syncytial virus.

2. The method of claim 1, wherein the sample comprising M2-1 protein is a sample comprising respiratory syncytial virus-infected cells.

3. The method of claim 1, wherein the sample comprising M2-1 protein comprises a purified respiratory syncytial virus M2-1 protein.

4. The method of claim 1, wherein the sample comprising M2-1 protein comprises M2-1 protein produced from a recombinant expression vector.

5. The method of claim 1, wherein the sample comprising M2-1 protein comprises cells producing M2-1 protein from a recombinant expression vector.

6. The method of claim 1, wherein the sample comprising M2-1 protein comprises an isolated respiratory syncytial virus.

7. The method of claim 1, wherein the sample comprising M2-1 protein is a sample comprising respiratory syncytial virus-infected animals.

8. A method of screening for potential antiviral compounds directed against respiratory syncytial virus (RSV), comprising the steps of:
   a) treating a sample comprising RSV M2-1 protein with a compound or chelator that inhibits zinc binding; and
   b) comparing an activity of M2-1 protein with the activity in an untreated sample, said M2-1 protein activity is selected from the group consisting of transcriptional antitermination by M2-1 protein, zinc binding of M2-1 protein, phosphorylation of M2-1 protein and M2-1 protein binding to respiratory syncytial virus N protein, wherein a decreased activity in the treated sample indicates said compound is potentially an antiviral compound directed against respiratory syncytial virus.

9. The method of claim 8, wherein the inhibition of zinc binding is mediated by a means selected from the group consisting of competing with zinc for binding to a $Cys_3$-$His_1$ motif within the M2-1 protein, preventing zinc from binding to a $Cys_3$-$His_1$ motif within the M2-1 protein, destroying formation of the $Cys_3$-$His_1$ motif and interfering with the interaction of the properly formed $Cys_3$-$His_1$ motif with its target.

10. The method of claim 8, wherein the sample comprising M2-1 protein is a sample comprising respiratory syncytial virus-infected cells.

11. The method of claim 8, wherein the sample comprising M2-1 protein comprises a purified respiratory syncytial virus M2-1 protein.

12. The method of claim 8, wherein the sample comprising M2-1 protein comprises M2-1 protein produced from a recombinant expression vector.

13. The method of claim 8, wherein the sample comprising M2-1 protein comprises cells producing M2-1 protein from a recombinant expression vector.

14. The method of claim 8, wherein the sample comprising M2-1 protein comprises an isolated respiratory syncytial virus.

15. The method of claim 8, wherein the sample comprising M2-1 protein is a sample comprising respiratory syncytial virus-infected animals.

* * * * *

SEQUENCE LISTING

```
<160> NUMBER OF SEQ ID NOS: 10

<210> SEQ ID NO 1
<211> LENGTH: 19
<212> TYPE: PRT
<213> ORGANISM: Unknown
<220> FEATURE:
<221> NAME/KEY: Domain
<222> LOCATION: 2..8, 10..14 and 16..18
<223> OTHER INFORMATION: Cys3-His1 zinc binding domain consensus
      sequence, Xaa at any position may be any amino acid

<400> SEQUENCE: 1

Cys Xaa Xaa Xaa Xaa Xaa Xaa Xaa Cys Xaa Xaa Xaa Xaa Xaa Cys
                 5                  10                  15

Xaa Xaa Xaa His

<210> SEQ ID NO 2
<211> LENGTH: 30
<212> TYPE: PRT
<213> ORGANISM: Artificial Sequence
```

```
<220> FEATURE:
<223> OTHER INFORMATION: wild-type M2 protein from respiratory
      syncytial virus

<400> SEQUENCE: 2

Met Ser Arg Arg Asn Pro Cys Lys Phe Glu Ile Arg Gly His Cys
                 5                  10                  15

Leu Asn Gly Lys Arg Cys His Phe Ser His Asn Tyr Phe Glu Trp
             20                  25                  30

<210> SEQ ID NO 3
<211> LENGTH: 30
<212> TYPE: PRT
<213> ORGANISM: Artificial Sequence
<220> FEATURE:
<223> OTHER INFORMATION: mutant M2 protein from respiratory
      syncytial virus

<400> SEQUENCE: 3

Met Ser Arg Arg Asn Pro Ser Lys Phe Glu Ile Arg Gly His Cys
                 5                  10                  15

Leu Asn Gly Lys Arg Cys His Phe Ser His Asn Tyr Phe Glu Trp
             20                  25                  30

<210> SEQ ID NO 4
<211> LENGTH: 30
<212> TYPE: PRT
<213> ORGANISM: Artificial Sequence
<220> FEATURE:
<223> OTHER INFORMATION: mutant M2 protein from respiratory
      syncytial virus

<400> SEQUENCE: 4

Met Ser Arg Arg Asn Pro Cys Gln Phe Glu Ile Arg Gly His Cys
                 5                  10                  15

Leu Asn Gly Lys Arg Cys His Phe Ser His Asn Tyr Phe Glu Trp
             20                  25                  30

<210> SEQ ID NO 5
<211> LENGTH: 30
<212> TYPE: PRT
<213> ORGANISM: Artificial Sequence
<220> FEATURE:
<223> OTHER INFORMATION: mutant M2 protein from respiratory
      syncytial virus

<400> SEQUENCE: 5

Met Ser Arg Arg Asn Pro Cys Lys Leu Glu Ile Arg Gly His Cys
                 5                  10                  15

Leu Asn Gly Lys Arg Cys His Phe Ser His Asn Tyr Phe Glu Trp
             20                  25                  30

<210> SEQ ID NO 6
<211> LENGTH: 30
<212> TYPE: PRT
<213> ORGANISM: Artificial Sequence
<220> FEATURE:
<223> OTHER INFORMATION: mutant M2 protein from respiratory
      syncytial virus

<400> SEQUENCE: 6

Met Ser Arg Arg Asn Pro Cys Lys Ser Glu Ile Arg Gly His Cys
                 5                  10                  15

Leu Asn Gly Lys Arg Cys His Phe Ser His Asn Tyr Phe Glu Trp
             20                  25                  30
```

```
<210> SEQ ID NO 7
<211> LENGTH: 30
<212> TYPE: PRT
<213> ORGANISM: Artificial Sequence
<220> FEATURE:
<223> OTHER INFORMATION: mutant M2 protein from respiratory
      syncytial virus

<400> SEQUENCE: 7

Met Ser Arg Arg Asn Pro Cys Lys Phe Gly Ile Arg Gly His Cys
                 5                  10                  15

Leu Asn Gly Lys Arg Cys His Phe Ser His Asn Tyr Phe Glu Trp
                20                  25                  30

<210> SEQ ID NO 8
<211> LENGTH: 30
<212> TYPE: PRT
<213> ORGANISM: Artificial Sequence
<220> FEATURE:
<223> OTHER INFORMATION: mutant M2 protein from respiratory
      syncytial virus

<400> SEQUENCE: 8

Met Ser Arg Arg Asn Pro Cys Lys Phe Gln Ile Arg Gly His Cys
                 5                  10                  15

Leu Asn Gly Lys Arg Cys His Phe Ser His Asn Tyr Phe Glu Trp
                20                  25                  30

<210> SEQ ID NO 9
<211> LENGTH: 30
<212> TYPE: PRT
<213> ORGANISM: Artificial Sequence
<220> FEATURE:
<223> OTHER INFORMATION: mutant M2 protein from respiratory
      syncytial virus

<400> SEQUENCE: 9

Met Ser Arg Arg Asn Pro Cys Lys Phe Glu Ile Arg Gly His Ser
                 5                  10                  15

Leu Asn Gly Lys Arg Cys His Phe Ser His Asn Tyr Phe Glu Trp
                20                  25                  30

<210> SEQ ID NO 10
<211> LENGTH: 30
<212> TYPE: PRT
<213> ORGANISM: Artificial Sequence
<220> FEATURE:
<223> OTHER INFORMATION: mutant M2 protein from respiratory
      syncytial virus

<400> SEQUENCE: 10

Met Ser Arg Arg Asn Pro Cys Lys Phe Glu Ile Arg Gly His Cys
                 5                  10                  15

Leu Asn Gly Lys Arg Cys His Phe Ser Ser Asn Tyr Phe Glu Trp
                20                  25                  30
```